United States Patent [19]

Masuho et al.

[11] 4,357,273
[45] Nov. 2, 1982

[54] ANTITUMOR PROTEIN HYBRID AND PROCESS FOR THE PREPARATION THEREOF

[75] Inventors: Yasuhiko Masuho; Naoji Umemoto, both of Hino; Takeshi Hara, Hachioji; Hidematsu Hirai, 9-5, Sakaigawa 3-chome, Chuo-ku, Sapporo-shi, Hokkaido, all of Japan

[73] Assignees: Teijin Limited, Osaka; Hidematsu Hirai, Hokkaido, both of Japan

[21] Appl. No.: 170,393

[22] Filed: Jul. 21, 1980

[30] Foreign Application Priority Data

Jul. 19, 1979 [JP] Japan .................. 54-90934

[51] Int. Cl.³ .................. C07C 103/52; A61K 37/00
[52] U.S. Cl. .................. 260/112.5 R; 424/177; 260/112 R
[58] Field of Search .................. 260/112.5 R, 112 R; 424/177

[56] References Cited

U.S. PATENT DOCUMENTS 4,160,018  7/1979  Bjorklund .................. 260/112.5 R
4,160,019  7/1979  Bjorklund .................. 260/112.5 R
4,201,770  5/1980  Stevens .................. 260/112.5 R Primary Examiner—Delbert R. Phillips
Attorney, Agent, or Firm—Sughrue, Mion, Zinn, Macpeak & Seas

[57] ABSTRACT

Antitumor protein hybrid, composed of a moiety which is substantially the fragment Fab of an anti-α-fetoprotein antibody and a moiety which is substantially the fragment A of a diphtheria toxin, which is expressed by the following formula (I):

$$\text{Fab}-(S_1-(X)_n-S_2-FA)_m \qquad (I)$$

(where Fab indicates a moiety which is substantially the fragment Fab of an anti-α-fetoprotein antibody; FA indicates a moiety which is substantially the fragment A of diphtheria toxin; X indicates a divalent organic radical; $S_1$ and $S_2$ are both sulfur atoms, $S_1$ indicating a sulfur atom arising from the disulfide bond (—S—S— bond) in an anti-α-fetoprotein antibody and $S_2$ a sulfur atom arising from the disulfide bond in a diphtheria toxin; n stands for 0 or 1 and m stands for an integer of 1 to 5). This antitumor protein hybrid has remarkable and specific citotoxicity against tumor cells.

9 Claims, 5 Drawing Figures (a)

(b)

(c)

FRAGMENT A          FRAGMENT B

ANTITUMOR PROTEIN HYBRID AND PROCESS FOR THE PREPARATION THEREOF

BACKGROUND OF THE INVENTION

1. Field of the Invention

The present invention relates to a novel antitumor protein hybrid, for example, cytotoxic against mouse tumors, and a process for the preparation thereof. More particularly, the present invention relates to a novel protein hybrid, which has a moiety which is substantially the fragment Fab of an anti-α-fetoprotein antibody and a moiety which is substantially the fragment A of a diphtheria toxin, is specifically useful as a remedy for malignant tumor e.g., in mice, and a process for the preparation of the same.

2. Description of the Prior Art

Many studies have been made on tumor-associated antigens and extensive research has especially been made with regard to the production of α-fetoprotein by liver cancer cells (Protein, Nucleic Acid, Enzyme, Vol.23, pp.579–593, 1978). In the body of an ordinary man, α-fetoprotein is, though formed during his fetal period, scarcely detected after his birth. However, when he suffers from liver cancer, its production takes place again in his body and its concentration in the blood reaches as high as 1,000 times the normal value. α-Fetoprotein is obtained from ascites fluid of a liver cancer patient and is purified by biochemical and immunochemical methods. Its properties are similar to those of serum albumin. It is a protein having a molecular weight of 70,000 and a isoelectric point of 4.5 to 5.0; however, its antigenicity is quite different from that of serum albumin. Therefore, it is possible to obtain an antibody (anti-α-fetoprotein antibody) specific Bind only to α-fetoprotein, by immunizing horses, cows, goats, sheep, monkeys or rabbits, etc. with purified α-fetoprotein. The antibody thus obtained binds to a cancer cell which produces α-fetoprotein; however, this specific binding can display only a slight cytotoxic activity against liver cancer cells. Accordingly, the present inventors discovered that a novel protein hybrid, which has a specific and strong cytotoxic activity against liver cancer cells, can be obtained by coupling an anti-α-fetoprotein antibody with fragment A of diphtheria toxin which has a strong cytotoxicity.

Several reports have been made on research for obtaining agents with selective cytotoxicity against cancer cells by conjugating an antitumor drug or a toxin to an antitumor antibody. Though no attempt has been made as to the use of an anti-α-fetoprotein antibody, some research has been made with the use of a diphtheria toxin as shown in the following examples.

For instance, F. L. Moolten et al. report that they prepared a conjugate by conjugating rabbit anti-SV40-transformed hamster sarcoma or lymphoma antibody to diphtheria toxin with glutaraldelyde as a coupling agent and were able to protect hamsters challenged with SV40-transformed tumors by administering the conjugate to hamsters (Journal of the National Cancer Institute, Vol.55, pp.473–477, 1975).

P. E. Thorpe et al. report that the conjugate prepared by coupling diphtheria toxin to antilymphocytic antibody by means of chlorambucil greatly reduced the protein synthesis of human lymphoblastoid cells, CLA4. (Nature, Vol.271, pp.752–754, 1978).

The results of these studies show that a conjugate of diphtheria toxin and antibody displays toxicity against the tumor cells selectively. However, these conjugates, when used as an antitumor drug, are believed to have some disadvantages as cited below. First, xenogeneic antibody (immunoglobulin) has a strong antigenicity in the human body and induces the formation of anti-xenogeneic immunoglobulin antibody which deactivates the antitumor activity and further causes an anaphylaxis shock. The second of the disadvantages is that the non-specific toxicity of diphtheria toxin is not nullified. More particularly, the object of these methods is to concentrate diphtheria toxin on the surface of tumor cells by the aid of antitumor antibody; however, since the conjugate contains the whole molecule of diphtheria toxin in its composition, it is apt to bind to normal cell surface receptors for diphtheria toxin and display cytotoxicity against the normal cells. Thirdly comes the defect which is found in the method of cross-linking the antibody with the diphtheria toxin. Many of the cross-linking agents such as glutaraldehyde, toluene diisocyanate, chlorambucil, etc. effect the cross-linking not only between the antibody and the toxin but also between the antibody and the antibody, and the toxin and the toxin, and moreover, they effect the formation of intra-molecule bonds in the antibody and in the toxin molecule, thus causing the formation of undesirable products and decrease or loss of the antitumor activity.

SUMMARY OF THE INVENTION

Based upon the idea mentioned above, the present inventors have achieved this invention as a result of earnest research work to develop an antitumor substance which displays strong, selective cytotoxicity against cancer cells producing α-fetoprotein.

The present invention relates to an antitumor protein hybrid, composed of a moiety which is substantially the fragment Fab of an anti α-fetoprotein antibody and a moiety which is substantially the fragment A of a diphtheria toxin, which is expressed by the following formula (I):

$$\text{Fab}-S_1-(X)_n-S_2-\text{FA}_m \qquad (I)$$

(where Fab indicates a moiety which is substantially the fragment Fab of an anti α-fetoprotein antibody; FA indicates a moiety which is substantially the fragment A of a diphtheria toxin; X indicates a divalent organic radical; $S_1$ and $S_2$ are both sulfur atoms, $S_1$ indicating a sulfur atom arising from the —S—S— bond in an anti α-fetoprotein antibody and $S_2$ a sulfur atom arising from the —S—S— bond in a diphtheria toxin; n stands for 0 or 1 and m stands for an integer of 1 to 5), and a process for preparing said antitumor protein hybrid, which process comprises binding the sulfur atom in said fragment Fab with the sulfur atom in said fragment A directly or indirectly.

DESCRIPTION OF THE PREFERRED EMBODIMENTS

What is called an anti-α-fetoprotein antibody in the present invention is an immunoglobulin which contains an anti-α-fetoprotein antibody prepared from the serum obtained from such animals as monkeys, horses, cows, goats, sheep, rabbits, etc. which are hyperimmunized with α-fetoprotein according to a publicly known method such as the Cohn ethanol fractionation method, ammonium sulfate fractionation method, ion-exchange chromatography, etc., or is an antibody further purified by affinity chromatography conducted over carriers with which α-fetoprotein is combined. Or it is a protein having an antibody activity of high selectivity to α-fetoprotein obtained from a culture fluid of hybridomas or from a serum or ascites of animals inoculated with hybridomas which are prepared by allowing antibody-producing lymphocytes obtained from an animal immunized with α-fetoprotein to fuse, for instance, with myeloma cells [See, for instance, G. Köhler and C. Milstein, Nature (London), 256, 495–497 (1975)].

Figure 1:
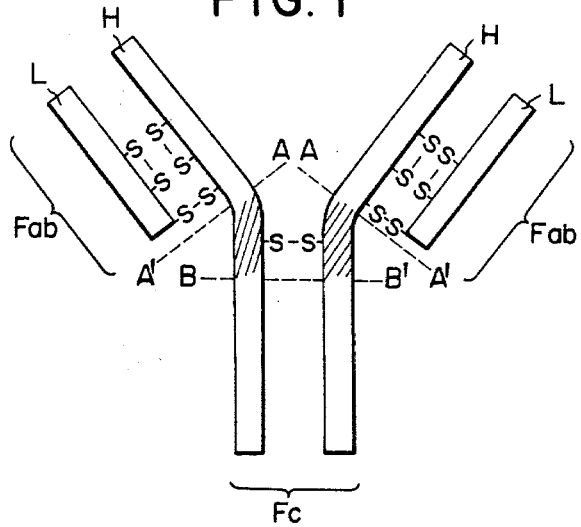
FIG. 1 is a pictorial drawing of a type specimen to show a basic structure of the immunoglobulin.

The basic structure of an immunoglobulin, which is a mixture of antibodies against various antigens including α-fetoprotein, comprises, as shown by a pictorial drawing of a type specimen in FIG. 1, two L chains which are indicated by L in the figure and two H chains indicated likewise by H, all chains being bound with at least three disulfide bonds (—S—S— bonds). To explain the basic structure of the immunoglobulin shown in FIG. 1, it consists of two Fab parts which are shown by Fab in the figure and Fc part shown by Fc; Fab part has an antibody activity (in the present invention, it means an activity to couple to α-fetoprotein), or more particularly a nature to selectively couple to the antigen; Fc part has a nature to couple to a complement or Fc receptor on the cell membrane.

The moiety substantially comprising the fragment Fab which is one of the moiety of the antitumor protein hybrid of the present invention corresponds to the moiety comprising the fragment having an antibody activity (a nature to recognize and couple to an antigen) arising from said Fab part of the immunogloblin. For instance, when immunogloblin is subjected to papain digestion in the presence of cystine, it is cleaved on the broken lines A-A' into two Fab fragments and one Fc fragment as shown in FIG. 1, and the Fab fragments thus obtained can be used as fragment Fab in the present invention. When the immunogloblin is treated with pepsin, it is cleaved on the broken line B-B' as shown in FIG. 1, to produce a dimer, (F(ab')₂), of Fab' part consisting of the Fab part and the hinge part which is shaded with oblique lines in the figure. Two Fab' fragments can also be obtained by cleaving the disulfide bond in the hinge part reductively, for instance, with the use of a thiol reagent or cleaving it by means of sulfonation with sulfite ions. Since this Fab' fragment has an antibody activity like Fab fragment (though it does not have the ability to couple to complements), it can be used as fragment Fab of the present invention. In the present invention, so far as the fragment Fab has an antibody activity, said Fab fragment or Fab' fragment may be the one chemically modified.

The thus obtained fragment Fab is used for the preparation of antitumor protein hybrid according to the present invention just as it is so far as it has at least one thiol radical (-SH) and/or S-sulfo radical (—S—$SO_3^-$) in the fragment but in other cases it is used after it has been changed into a fragment having at least one thiol radical and/or S-sulfo radical by cleaving at least one of the disulfide bonds in the chain (in the H chains or the L chains) and the disulfide bonds between the chains (between the H chain and the L chain) according to a publicly known method. The number of the thiol radicals and/or S-sulfo radicals in the fragment Fab should preferably be in the range of 1–5 (corresponding to m=1–5 in the formula (I)) and it is especially preferable to have the number of the thiol radicals and/or S-sulfo radicals which are formed by cleaving the bonds between the chains within the range of 1–2 (corresponding to m=1–2 in the formula (I)).

Figure 2:
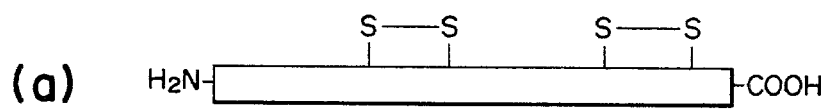
FIG. 2 presents pictorial drawings of a type specimen of diphtheria toxin, wherein (a) shows a structure of intact toxin, (b) shows a structure of nicked toxin, and (c) shows structures of fragment A and fragment B.
Figure 2:
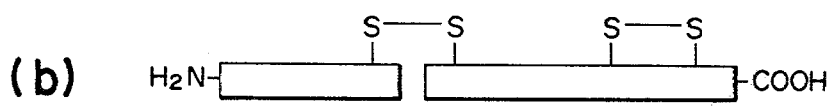
Figure 2:
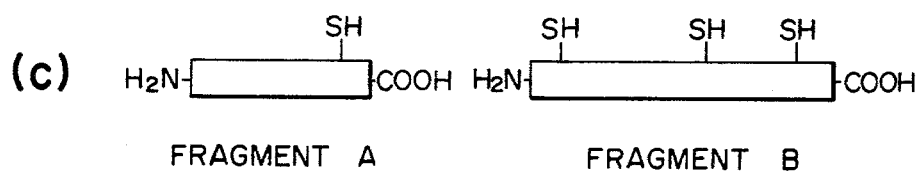

What is called diphtheria toxin in the present invention is a protein toxin produced by Corynebacterium diphtheriae or its mutants. For instance, a diphtheria toxin produced by Corynebacterium diphtheriae consists of a single polypeptide chain having a molecular weight of about 62,000–63,000 and this is called an intact toxin. The intact toxin has two disulfide bonds (—S—S bonds) in its molecule as shown in a pictorial drawing of a type specimen of FIG. 2, (a). When this intact toxin is treated under moderate conditions with such a proteolytic enzyme as trypsin, there occurs a separation at a specific point in the disulfide bond nearer to the amino-terminal to form a nicked toxin as shown in FIG. 2, (b). When this nicked toxin is treated with a reducing agent, it is divided into fragment A having a molecular weight of about 24,000 and fragment B having a molecular weight of about 38,000–39,000 as shown in FIG. 2, (c). Cleavage of the nicked toxin into fragment A and fragment B can also be conducted by means of sulfonation with sulfite ions, and in this case the thiol radical of fragment A thus obtained is in the form of the S-sulfo radical (—S—$SO_3^-$). The intact toxin has a very strong toxicity against animals; however, fragment A and fragment B themselves are both nontoxic. On the other hand, the intact toxin has no adenosine diphosphate (ADP)-ribose transferase activity on the elongation factor 2 (EF-2) defined below, while fragment A has the transferase activity. And though fragment B has no transferase activity, it has the capability of coupling to a cell receptor which fragment A does not possess.

In the present invention, the moiety substantially comprising fragment A which is one of the moieties of the antitumor protein hybrid means a moiety composed of a fragment of the diphtheria toxin which satisfies the aforementioned characteristics of fragment A, namely the following two characteristics:

(1) To have ADP-ribose transferase activity on EF-2.
(2) To have no capability of coupling to a cell receptor and no cytotoxicity by itself.

So far as the abovementioned two requirements are satisfied, the nontoxic protein produced by a mutant (which has one disulfide bond in the molecule) such as CRM 30 and CRM 45 produced, for instance, from Corynebacterium diphtheriae mutant such as C₇ (β30) and C₇ (β45) and fragment obtained by treating them under moderate conditions which trypsin in the presence of such a reducing agent as thiol reagent are included in fragment A of the present invention.

When the thus obtained fragment Fab has at least one thiol radical (-SH) and/or S-sulfo radical ($-S-SO_3^-$), it is used for the preparation of antitumor protein hybrid according to the present invention just as it is or after the S-sulfo radical has been reduced to a thiol radical. In other cases, it is used after it has been changed into a fragment having at least one thiol radical or S-sulfo radical by cleaving at least one disulfide bond in the fragment according to a publicly known method. As for fragment A in the present invention, a fragment having one thiol radical or S-sulfo radical in the molecule is especially preferable.

Incidentally, the ADP-ribose transferase activity on EF-2 is defined as follows.

EF-2 is known as a protein elongation factor which is related with protein synthesis of cells and fragment A of the diphtheria toxin deactivates EF-2 by catalytically promoting the reaction mentioned below between EF-2 and nicotinamide-adeninedinucleotide (NAD):

$$EF\text{-}2 + NAD^+ \rightarrow (ADP\ ribose)\text{-}(EF\text{-}2) + nicotinamide + H^+$$

The performance to promote this reaction is defined as ADP-ribose transferase activity on EF-2.

ADP-ribose transferase activity on EF-2 acts to interfere with protein synthesis and works as the entity of lethaltoxicity for animals; however, it is necessary for fragment A of the diphtheria toxin which has this ADP-ribose transferase activity on EF-2 to have fragment B which is capable of coupling to a cell receptor in order that fragment A enters into the cell and exerts its cytocidal effect: fragment A alone can not cause death in animals.

In the present invention, when fragment Fab of anti-α-fetoprotein antibody having at least one thiol radical and/or S-sulfo radical in the fragment is made to react directly with fragment A of the diphtheria toxin having at least one thiol radical and/or S-sulfo radical in the fragment under the reaction conditions mentioned later, antitumor protein hybrids expressed by the undermentioned formula (I') which corresponds to the aforementioned formula (I) wherein $n=0$ are obtained.

$$Fab-S_1-S_2-FA)_m \quad (I')$$

(where the definitions of Fab, FA, m, $S_1$ and $S_2$ are the same as those given in case of formula (I)). Of these, the one which has a structure expressed by the following formula (II) is especially preferable from the viewpoint of ease of preparation, separation and purification:

$$Fab-S_1-S_2-FA)_p \quad (II)$$

(where definitions of Fab, FA, $S_1$ and $S_2$ are the same as those given in case of formula (I): p indicates 1 or 2).

In the present invention, the divalent organic radical, which is expressed by X where $n=1$ in the aforementioned formula (I), means an organic radical arising from a cross-linking agent having in the molecule at least two functional groups capable of forming a sulfide bond (—S— bond) by reacting with a thiol radical (-SH). Such cross-linking agents involve, for instance, a bismaleimide compound which is expressed by the undermentioned formula (III), bishalocarbonyl compound which is expressed by the formula (IV), dihaloketone compound expressed by the formula (V), and halocarbonylmaleimide compound expressed by the formula (VI):

$$\text{(III)}$$

(where Y indicates a divalent organic radical).

$$X_1-CH_2-\underset{\underset{O}{\|}}{C}-Z-\underset{\underset{O}{\|}}{C}-CH_2-X_2 \quad (IV)$$

(where Z indicates a divalent organic radical, $X_1$ and $X_2$ are the same or differ from each other indicating bromine or iodine).

$$X_1-CH_2COCH_2-X_2 \quad (V)$$

(where $X_1$ and $X_2$ are the same or differ from each other indicating bromine or iodine).

$$\text{(VI)}$$

(where W indicates a divalent organic radical and $X_1$ indicates bromine or iodine).

Specific examples of bismaleimide compound expressed by the abovementioned formula (III) are, for instance, N,N'-(1,2-phenylene)-dimaleimide, N,N'-(1,4-phenylene)dimaleimide, 4,4'-bis(maleoylamino)azobenzene, and bis(N-maleimidomethyl)ether. Specific examples of bishalocarbonyl compound expressed by the formula (IV), are N,N'-alkylenebis(bromoacetamide) and N,N'-alkylenebis(iodoacetamide) (wherein the alkylene radical has 2–15 carbon atoms). As for specific examples of dihaloketone compound expressed by the formula (V), are 1,3-dibromoacetone and 1,3-diiodoacetone. Specific examples of halocarbonylmaleimide compound expressed by the formula (VI), there are N-(α-bromoacetoxymethyl)maleimide and N-(α-iodoacetoxymethyl) maleimide.

The antitumor protein hybrid of the present invention can be prepared according to the methods given in the following.

(1) A method either to make a substantial fragment Fab which has at least one S-sulfo radical in the fragment react with a substantial fragment A which has at least one thiol radical in the fragment or to make a substantial fragment Fab which has at least one thiol radical in the fragment react with a substantial fragment A which has at least one S-sulfo radical in the fragment.

In these methods, it is preferable to use a ratio of 0.3–3 moles of fragment A to 1 mole of fragment Fab. The reaction can be conducted by mixing fragment Fab and fragment A in a buffer solution whose pH is in the range of 6 to 10 to a total protein concentration of 0.5 to 100 mg/ml (more preferably 1 to 20 mg/ml) and leaving the mixture at 0° to 60° C. or dialyzing the reaction mixture against a buffer solution having the same pH value as the reaction mixture. The reaction time generally extends over a period of four hours to three days, depending upon the scale and conditions of the reaction. The separation of the hybrid thus composed of fragment Fab and fragment A from the reaction mixture and the purification can be carried out by a usual procedure, for instance, of dialysis or column chromatography of a molecular sieve effect.

The method mentioned above allows the reaction to proceed smoothly under very moderate conditions to produce a highly purified hybrid. The method also has the advantage of permitting the selective formation of hybrid composed of fragment Fab and fragment A (as compared to the formation of a hybrid between fragments Fab themselves or between fragments A themselves linked by the disulfide bond).

(2) A method for binding a substantial fragment Fab which has at least one thiol radical in the fragment and a substantial fragment A which has at least one thiol radical in the fragment with the use of any of the aforementioned cross-linking agents expressed by the formula (III), (IV), (V) or (VI).

In the above method, the reaction can be conducted by bringing the fragment Fab, cross-linking agent and fragment A into contact with each other simultaneously. However, it is preferable to carry out the preparation of the hybrid by making fragment A react with the reaction product obtained by first allowing fragment Fab to react with the cross-linking agent or by making fragment Fab react with the reaction product obtained by first allowing fragment A to react with the cross-linking agent. In the former case, it is preferable to use 0.8–6 moles of the cross-linking agent and fragment A respectively to 1 mole of fragment Fab. In the latter case, it is preferable to use 0.8–3 moles of the cross-linking agent and 0.2–3 moles of fragment Fab to 1 mole of fragment A. The reaction is started at 0° to 60° C. with stirring with the addition of the cross-linking agent dissolved in a small amount of solvent such as N,N-dimethylformamide, dimethyl sulfoxide, 1,2-dimethoxyethane, methanol, ethanol, acetone, etc. to a solution of fragment Fab or fragment A buffered at a pH of 6 to 10 (the protein concentration being preferably controlled to 0.5 to 100 mg/ml, or more preferably to 1 to 20 mg/ml). After the removal of the cross-linking agent left unreacted by means of dialysis or column chromatography of a molecular sieve effect, another fragment solution buffered at a pH of 6 to 10 (the preferable ranges of protein concentration being the same as mentioned above) is added to carry out the reaction at 0° to 60° C. The separation, and purification as well, of the thus obtained hybrid of fragment Fab and fragment A from the reaction mixture can be effected according to a usually adopted method such as column chromatography of the molecular sieve effect.

(3) A method in which fragment Fab of an anti-α-fetoprotein antibody which has at least one thiol radical in the fragment and fragment A of a diphtheria toxin which has at least one thiol radical in the fragment are subjected to an oxidative reaction in the presence of each other to have them both bound by the disulfide bond. As for the oxidative reaction, any of an air oxidation method, method of oxidation using o-iodobenzoic acid and method in which oxidation is effected in the system of o-phenanthroline and cupric sulfate may be adopted.

(4) A method in which either fragment Fab or fragment A which has at least one thiol radical in the fragment is first made to react with Ellman's reagent, 4,4'-dithiodipyridine, 2,2'-dithiodipyridine, or tetrathionate and the reaction product thus obtained is then made to react with another of the above fragments.

The antitumor protein hybrid of the present invention consists of a moiety substantially comprising fragment A which demonstrates toxicity against mice tumor cells of liver cancer, etc. producing α-fetoprotein, when internalized into the cells, and a moiety substantially comprising fragment Fab which specifically recognizes the tumor cell and works as a carrier to guide the fragment A to the tumor cell and take fragment A into the cell as well and this hybrid has excellent characteristics mentioned below.

(1) Since the hybrid of the present invention does not contain the Fc part of the immunoglobulin, non-specific binding to Fc receptors on the cell membrane with the Fc part is avoided and this fact allows the antibody activity or performance of the fragment Fab to selectively couple to tumor cells which are productive of α-fetoprotein.

(2) It is known that, when a xenogenic immunoglobulin is used, it is the Fc part that has the strongest antigenicity. In case of the hybrid according to the present invention, since it does not contain the Fc part of the immunoglobulin, the antigenicity of the xenogeneic immunoglobulin is reduced remarkably.

(3) It is known that, in case of diphtheria toxin, it is the fragment B that has the nature to couple to the receptor of cells (normal cells and tumor cells) and that the fragment A can be taken into the cell by means of the coupling of the fragment B to the cell membrane to demonstrate cytotoxicity. However, since the hybrid of the present invention does not contain the fragment B, the hybrid of the present invention is not cytotoxic to normal cells. Furthermore, since it does not contain the fragment B, the antigenicity of the diphtheria toxin is also reduced.

(4) The hybrid of the present invention has a moiety substantially comprising the fragment Fab obtained from the anti-α-fetoprotein antibody and this moiety specifically recognizes a tumor cell producing of α-fetoprotein and make the tumor cell take in specifically the moiety substantially comprising the fragment A of the diphtheria toxin. The fragment A thus taken in demonstrates a remarkable cytotoxicity to the tumor cell.

The present invention is described in detail by the following examples.

EXAMPLE 1

[(a) Preparation of fragment Fab' of anti-α-fetoprotein antibody]

Serum was separated from the blood drawn from a horse hyperimmunized with α-fetoprotein. The serum was subjected to affinity chromatography on a column of carriers with which α-fetoprotein was combined to obtain a pure anti-α-fetoprotein antibody. 5 mg of pepsin was added to 4.2 ml of an antibody solution (23 mg/ml, 0.02 M acetate buffer, pH 4.0) and the pepsin digestion was carried out at 37° C. for 20 hours. To this solution, 1 M trishydroxyaminomethane was added dropwise until the solution was neutralized. The solution was put to column chromatography (column size, 2.8 cm×108 cm) on Sephadex G200 equilibrated with saline to obtain fractions of F(ab')$_2$ fragment, which fractions were collected together and condensed. 0.5 ml of the thus obtained F(ab')$_2$ solution (10 mg/ml) was dialyzed against 1 l of 0.01 M tris buffer (pH 8.1) containing 0.14 M sodium chloride and 2 mM ethylenediaminetetraacetic acid and subjected to reduction at 37° C. for 1 hour with added 2-mercaptoethanol (the final concentration of 2-mercaptoethanol being 2 mM). The reaction solution was further dialyzed against 3 l of 5 mM acetate buffer (pH 5.5) containing 0.14 M sodium chloride to obtain a fragment Fab' solution (having one thiol radical arising from a disulfide bond at the hinge part).

[(b) Preparation of fragment A of diphtheria toxin]

0.15 ml of a trypsin solution having a concentration of 0.1 mg/ml was added to 18.5 ml of an aqueous solution (pH 8.3) of 0.05 M Tris.HCl-2 mM ethylenediaminetetraacetic acid containing 210 mg of diphtheria toxin, and the digestion was carried out at 25° C. for 50 minutes. After that 0.3 ml of a soybean trypsin inhibitor solution having a concentration of 0.5 mg/ml was added thereto to stop the reaction. Urea (final concentration of 6 M), sodium sulfite (final concentration 0.168 M) and sodium tetrathionate (final concentration 0.042 M) were added to the obtained digestion product and the mixture was subjected to S-sulfonative cleavage at 37° C. for 2 hours. The resulting reaction solution was subjected to Sephadex G150 column chromatography (column size 3.5 cm×112 cm) over a solution (pH 5.3) of 6 M urea-0.03 M acetate buffer and only the fractions of fragment A which came out later were collected. These fractions were dialyzed against distilled water to give a pure fragment A solution (having one S-sulfo radical).

[(c) Preparation of antitumor protein hybrid]

Figure 3:
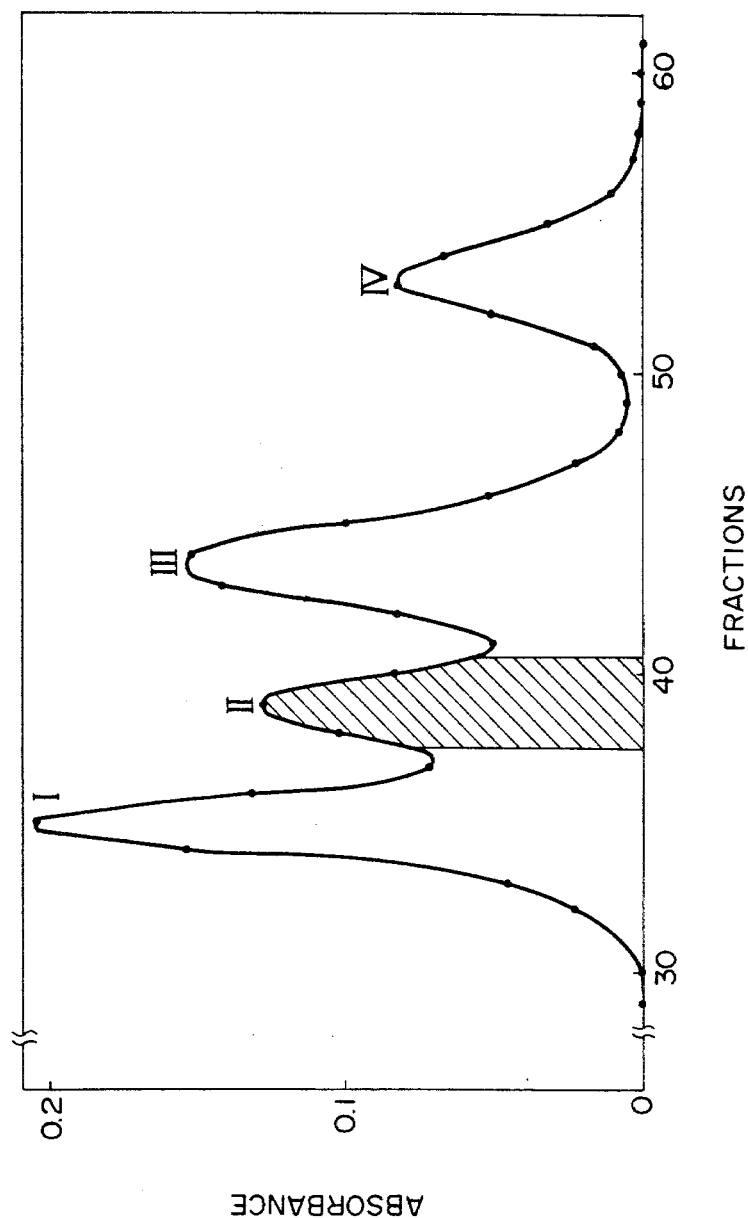
FIG. 3 shows the elution pattern of a reaction product of fragment Fab' of horse anti-α-fetoprotein antibody and fragment A of diphtheria toxin by column chromatography on Sephadex G 150 (superfine) and the shadowed portion contains the hybrid of the present invention.

A mixture consisting of the fragment Fab' solution (2.6 mg/ml, 0.9 ml) having a thiol radical obtained according to the aforementioned (a) and the fragment A solution (2.7 mg/ml, 0.45 ml) having a S-sulfo radical obtained according to the aforementioned (b) was dialyzed against 1 l of 0.05 M glycine buffer (pH 9.15) containing 0.1 M sodium chloride and 2 mM ethylenediaminetetraacetic acid at 4° C. for three days to effect the reaction to couple the two fragments. The obtained product was subjected to Sephadex G 150 (superfine) column chromatography (column size 1.6 cm×93 cm) equilibrated with saline to obtain 2.0 ml-fractions of effluent. The absorbance at 280 mμ was measured for each fraction to know the concentration of protein and the obtained result is shown in FIG. 3.

[(d) Analysis by means of sodium dodecyl sulfate-polyacrylamide gel electrophoresis (hereinafter referred to as SDS.PAGE)].

Figure 4:
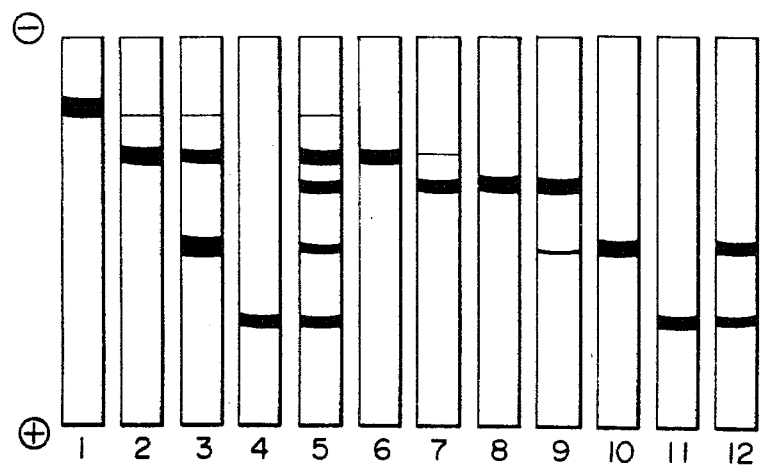
FIG. 4 shows patterns obtained from sodium dodecyl sulfate-polyacrylamide gel electrophoresis. Test substances of the respective disks are shown in Example 1, (d).
Figure 5:
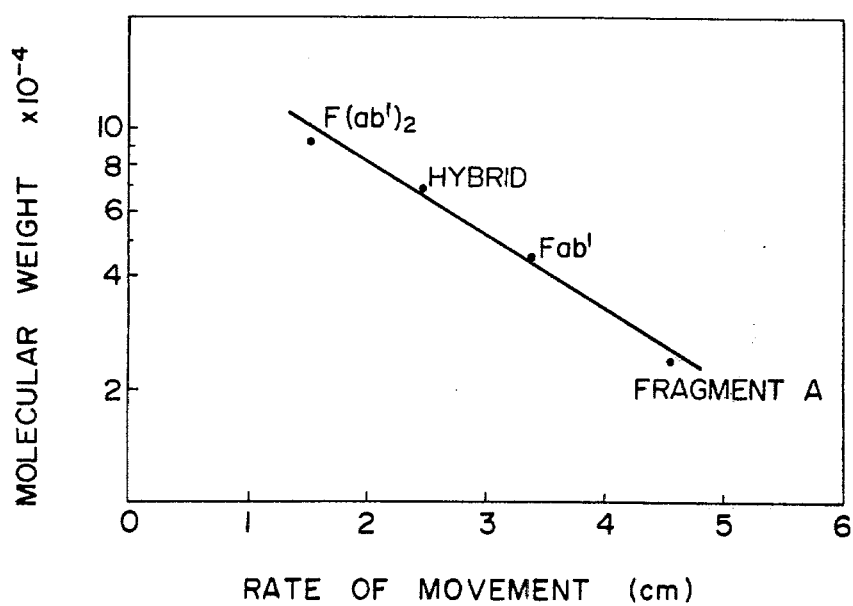
FIG. 5 shows the relationship between the rate of movement in electrophoresis and the molecular weight of the protein.

SDS.PAGE was conducted with a gel concentration of 5.6% according to the method of Weber and Osborn (K. Weber and M. Osborn, J. Biol. Chem., VOL 244, pp.4406-4412, 1969). The results are shown in FIG. 4. In FIG. 4, the lower end is the positive electrode and the upper end is the negative electrode. In the measurement by means of electrophoresis, the protein having a smaller molecular weight shows a higher rate of movement. Disc 1, immonogloblin; disc 2, fragment F(ab')$_2$; disc 3, fragment Fab' in which unreduced fragment F(ab')$_2$ is also detected; disc 4, fragment A; disc 5, reaction mixture of fragment Fab' and fragment A; disc, 6 the 35th fraction of FIG. 3; disc 7, the 38th fraction; disc 8, the 39 fraction; disc 9, the 40th fraction; disc 10, the 44th fraction; disc 11, the 53rd fraction; disc 12, the 39th fraction moderately reduced. In FIG. 3, the four peaks are named Peaks I, II, III, and IV from the left to the right and it is understood that Peak I is fragment F(ab')$_2$ as is clear from disc 6, Peak III is fragment Fab' as is clear from disc 10, and Peak IV is fragment A as is clear from disc 4. Peak II is a reaction product, which should be either the dimer of fragment A or the hybrid Fab'—S—S—A. When this product was moderately reduced with the use of 2 mM 2-mercaptoethanol, equimolar amounts of fragment Fab' and fragment A as known from disc 12 were generated. Accordingly, it was concluded that Peak II was the hybrid Fab'—S—S—A. As further shown in FIG. 5, when the rate of movement on SDS.PAGE and the molecular weight of proteins were plotted on a semilogarithmic graph, the obtained plots were linear and it was found that the measured value of the molecular weight of the hybrid was perfectly in accord with the calculated value.

[(e) Measurement of cytotoxicity of antitumor protein hybrid]

An aqueous solution of the protein hybrid of the present invention was obtained by mixing the fractions corresponding to peak II in FIG. 3. The cytotoxicity of the protein hybrid of the present invention against rat hepatoma cells AH 66 with the use of this aqueous solution (AH 66 is a cell which is capable of producing α-fetoprotein). 2×10$^4$ of AH 66 were suspended in 0.8 ml of the Eagle MEM medium containing 10% fetal calf serum. Four lots of this kind of cell suspension were prepared, to the first of which 0.2 ml of saline was added, to the second of which 0.2 ml of horse anti-α-fetoprotein IgG was added, to the third of which 0.2 ml of horse anti-α-fetoprotein F(ab')$_2$, and to the fourth of which 0.2 ml of the protein hybrid of the present invention was added and the respective suspensions were subjected to cultivation in an atmosphere of 5% CO$_2$ at 37° C. for 68 hours. After the culturing was over, the cells were treated with 0.25% trypsin solution to give uniform cell suspensions and then were subjected to 0.3% Trypan Blue supravital staining to dye the dead cells to determine the number of the viable cells under the microscope. The results are shown in Table 1.

TABLE 1

| | Cytotoxicity of antitumor protein hybrid against AH 66 | |
|---|---|---|
| | Number of viable AH 66 cells after 68-hour culture | Control of proliferation (%) |
| 1. Saline | 1.51 × 10$^5$ | 0 |
| 2. IgG* | 1.23 × 10$^5$ | 21.4 |
| 3. F(ab')$_2$* | 1.20 × 10$^5$ | 23.7 |
| 4. Protein hybrid* | 0.47 × 10$^5$ | 79.4 |

*Each sample was added to make the final concentration of 100 μg/ml.

Table 1 has made it clear that the initial $2\times10^4$ cells increased to as many as $1.5\times10^5$ when saline was added to the culture fluid, while the number of cells increased only to $0.47\times10^5$ to show that the inhibition of proliferation was about 80% when the protein hybrid of the present invention was added at a concentration rate of 100 μg/ml. On the other hand, when IgG and F(ab')$_2$ were added respectively at the same concentration, both cases showed only about 20% efficiency of inhibiting proliferation.

EXAMPLE 2

[(a) Preparation of fragment Fab' of anti-α-fetoprotein]

21 mg of sodium sulfite and 13 mg of sodium tetrathionate were added to 3 ml saline containing 29 mg of the dimer of fragment Fab' of horse anti-α-fetoprotein antibody prepared according to Example 1, (a), and after the mixture was subjected to S-sulfonative cleavage at 37° C. for one hour to obtain fragment Fab' having an S-sulfo radical, the reagents were removed by dialysis.

[(b) Preparation of fragment A of diphtheria toxin]

0.05 ml of 0.5 M aqueous solution of 2-mercaptoethanol was added to 1 ml of a solution of fragment A (4.8 mg/ml) obtained by dialyzing the solution of fragment A having one S-sulfo radical of diphtheria toxin prepared according to Example 1, (b), against an aqueous solution (pH 8.3) of 0.01 M Tris.HCl—0.14 M sodium chloride—2 mM ethylenediaminetetraacetic acid, and the reduction was continued at 37° C. for 1 hour. After that, 2-mercaptoethanol was removed by means of dialysis to obtain fragment A having one thiol radical.

[(c) Preparation of antitumor protein hybrid]

2 ml of an aqueous solution containing 5.8 mg of fragment Fab' prepared in the aforementioned (a) and 3.2 mg of fragment A prepared in the preceding (b) was prepared. This solution was dialyzed at 4° C. for three days against 1 l of an aqueous solution (pH 9.15) of 0.05 M glycine buffer—0.10 M sodium chloride—2 mM ethylenediaminetetraacetic acid to carry out the reaction to link both fragments. The reaction was followed by the same procedure as taken in Example 1 to give the protein hybrid, which is the object of the present invention, having fragment Fab' and fragment A linked with a disulfide bond.

EXAMPLE 3

A fragment Fab' solution (7 mg/ml) was prepared by dissolving fragment Fab' of anti-α-fetoprotein immunoglobulin IgG having one thiol radical obtained in Example 1, (a) in a mixed solution consisting of 2 parts by volume of 0.1 M sodium phosphate buffer (pH 6.0) and 1 part by volume of acetone. A suspension of a cross-linking agent, N,N'-(1,4-phenylene)dimaleimide (PDM) in acetone (5 mg/ml) was separately prepared.

0.1 ml of the PDM suspension was added dropwise to 1.0 ml of the fragment Fab' solution and the reaction was allowed to proceed at room temperature for 30 minutes. The acetone in the reaction mixture was removed with the use of an evaporator and further undissolvable substances were removed by means of centrifugation conducted at 10,000 rpm for 30 minutes. The solution thus obtained was subjected to Sephadex G25 column chromatography equilibrated with 0.1 M sodium phosphate buffer (pH 6.0) to afford a solution of fragment Fab' having a PDM residue.

The solution of fragment Fab' having a PDM residue thus obtained was admixed with fragment A of diphtheria toxin having one thiol radical prepared according to Example 2, (b), in such a way to have the fragment Fab'-fragment A molar ratio of 1:2 and the coupling reaction was allowed to proceed at 4° C. for 24 hours and further at 37° C. for 1 hour. The obtained reaction solution was subjected to Sephadex G150 column chromatography under the same conditions as Example 1. The 38th and 39th fractions contained protein having a molecular weight of about 70,000 at a purity of 90%. This protein caused a precipitin line, in the antigen antibody reaction, with an antibody against horse immunoglobulin obtained by immunizing goats and it also caused a precipitin line with an antibody against diphtheria toxoid obtained by immunizing sheep. Therefore, it was understood that this protein is a hybrid of fragment Fab' of a horse anti-α-fetoprotein antibody and fragment A of a diphtheria toxin. Further it was confirmed that, in this protein, fragment Fab' and fragment A were not linked by a disulfide bond but cross-linked by PDM from the fact that the protein was not reductively cleaved into fragment Fab' and fragment A with 2-mercaptoethanol as determined on SDS.PAGE.

EXAMPLE 4

According to Example 3, antitumor protein hybrid was obtained, in which fragment Fab' and fragment A were linked by a cross-linking agent, N,N'-(1,2-phenylene)dimaleimide via the respective sulfur atoms, wherein N,N'-(1,2-phenylene)dimaleimide was used in the place of PDM which was used in Example 3.

EXAMPLE 5

According to Example 3, antitumor protein hybrid was obtained, in which fragment Fab' and fragment A were linked by a cross-linking agent, 4,4'-bis(-maleoylamino) azobenzene via the respective sulfur atoms, wherein 4,4'-bis(maleoylamino)-azobenzene was used in the place of PDM which was used in Example 3.

EXAMPLE 6

Fragment Fab' of anti α-fetoprotein antibody having a thiol radical obtained according to Example 1, (a) was dissolved in a mixed solution consisting of 3 parts by volume of 0.1 M sodium phosphate buffer (pH 6.0) and 1 part by volume of N,N-dimethylformamide at the concentration of 7 mg/ml to prepare a solution of fragment Fab'. Besides this solution, a solution was prepared by dissolving a cross-linking agent, N,N'-ethylenebis(iodoacetamide), in N,N-dimethylformamide at a concentration of 6 mg/ml.

The reaction was carried out at room temperature for one hour by adding 0.1 ml of the N,N'-ethylenebis(iodoacetamide) solution dropwise to 1.0 ml of the fragment Fab' solution, to which reaction mixture 0.05 ml of 0.07 M aqueous solution of 2-mercaptoethylamine were added. The mixture was left standing at room temperature for 1 hour. The obtained mixed solution was purified by column chromatography on Sephadex G25 equilibrated with 0.1 M sodium phosphate buffer (pH 6.0) to give a solution of fragment Fab' having N,N'-ethylene-bis(iodoacetamide) residue.

The fragment A of diphtheria toxin having one thiol radical prepared according to Example 2, (b) was added to the solution of fragment Fab' having N,N'-ethylenebis(iodoacetamide) residue obtained as mentioned above to a molar ratio of fragment Fab' having the N,N-ethylenebis-(iodoacetamide) residue to fragment A of 1:2 and mixed. After that, the procedures were followed as in the case of Example 3 to give protein hybrid of the present invention in which fragment Fab' and fragment A were linked by a cross-linking agent, N,N'-ethylenebis(iodoacetamide) through the medium of the respective sulfur atoms.

EXAMPLE 7

According to Example 6, antitumor protein hybrid was obtained, in which fragment Fab' and fragment A were linked by a cross-linking agent, N,N'-hexamethylenebis(iodoacetamide) through the medium of the respective sulfur atoms, wherein N,N'-hexamethylenebis(iodoacetamide) was used in the place of N,N'-ethylenebis(iodoacetamide) which was used in Example 6.

EXAMPLE 8

According to Example 6, antitumor protein hybrid was obtained, in which fragment Fab' and fragment A were linked by a cross-linking agent, N,N'-undecamethylenebis(iodoacetamide) through the medium of the respective sulfur atoms, wherein N,N'-undecamethylenebis(iodoacetamide) was used in the place of N,N'-ethylenebis(iodoacetamide) which was used in Example 6.

EXAMPLE 9

According to Example 3, antitumor protein hybrid was obtained, in which fragment Fab' and fragment A were linked by a cross-linking agent, bis(N-maleimidemethy)ether through the medium of the respective sulfur atoms, wherein bis(N-maleimidemethyl)ether was used in the place of PDM which was used in Example 3.

What is claimed is:

1. Antitumor protein hybrid comprising (1) a moiety which is substantially the fragment Fab of an anti-α-fetoprotein antibody and (2) a moiety which is substantially the fragment A of a diphtheria toxin, which antitumor protein hybrid is expressed by the following formula (I):

Fab(S₁—(X)ₙ—S₂—FA)ₘ     (I)

where Fab indicates a moiety which is substantially the fragment Fab of an anti-α-fetoprotein antibody; FA indicates a moiety which is substantially the fragment A of diphtheria toxin; X indicates a pharmacologically inert divalent organic radical; $S_1$ and $S_2$ are both sulfur atoms, $S_1$ indicating a sulfur atom arising from the disulfide bond in the anti-α-fetoprotein antibody and $S_2$ a sulfur atom arising from the disulfide bond in the diphtheria toxin; n represents 0 or 1 and m represents an integer of 1 to 5.

2. Antitumor protein hybrid according to claim 1, which is expressed by the following formula (II):

Fab—S₁—S₂—FA)ₚ     (II)

where the definitions of Fab, FA, $S_1$ and $S_2$ are the same as those given in case of formula (I) and p represents 1 or 2.

3. Antitumor protein hybrid according to claim 1 or claim 2, wherein FA is a moiety derived from the fragment A of a diphtheria toxin.

4. Antitumor protein hybrid according to claim 1 or claim 2, wherein Fab is a moiety derived from the fragment Fab of an anti-α-fetoprotein antibody.

5. Antitumor protein hybrid according to claim 1 or claim 2, wherein Fab is a moiety derived from the fragment Fab' of an anti-α-fetoprotein antibody.

6. Antitumor protein hybrid according to claim 1, wherein X is a divalent organic radical arising from a dimaleimide compound which is expressed by the following formula (III):

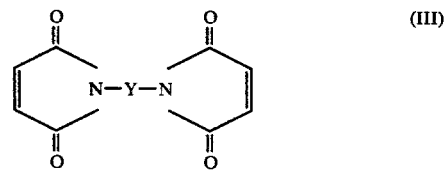

where Y indicates a divalent organic radical.

7. Antitumor protein hybrid according to claim 1, wherein X is a divalent organic radical arising from a bishalocarbonyl compound which is expressed by the following formula (IV):

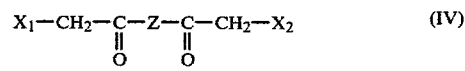

where Z indicates a divalent organic radical, and $X_1$ and $X_2$ are either the same or different from each other and represent bromine or iodine.

8. Antitumor protein hybrid according to claim 1, wherein X is a divalent organic radical arising from a dihaloketone compound which is expressed by the following formula (V):

X₁—CH₂—CO—CH₂—X₂     (V)

where $X_1$ and $X_2$ are either the same or different from each other and represent bromine or iodine.

9. Antitumor protein hybrid according to claim 1, wherein X is a divalent organic radical arising from a halocarbonyl maleimide compound which is expressed by the following formula (VI):

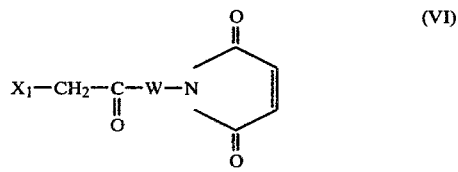

where W is a divalent organic radical and $X_1$ represents bromine or iodine.

* * * * *